United States Patent
Rosenbek et al.

(10) Patent No.: US 9,579,056 B2
(45) Date of Patent: Feb. 28, 2017

(54) SCREENING FOR NEUROLOGICAL DISEASE USING SPEECH ARTICULATION CHARACTERISTICS

(71) Applicants: University of Florida Research Foundation, Incorporated, Gainesville, FL (US); Board of Trustees of Michigan State University, East Lansing, FL (US)

(72) Inventors: John Clyde Rosenbek, Gainesville, FL (US); Mark D. Skowronski, Okemos, MI (US); Rahul Shrivastav, East Lansing, MI (US); Supraja Anand, East Lansing, MI (US)

(73) Assignees: University of Florida Research Foundation, Incorporated, Gainesville, FL (US); Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 14/435,969

(22) PCT Filed: Oct. 9, 2013

(86) PCT No.: PCT/US2013/064041
§ 371 (c)(1),
(2) Date: Apr. 15, 2015

(87) PCT Pub. No.: WO2014/062441
PCT Pub. Date: Apr. 24, 2014

(65) Prior Publication Data
US 2015/0265205 A1 Sep. 24, 2015

Related U.S. Application Data

(60) Provisional application No. 61/714,434, filed on Oct. 16, 2012.

(51) Int. Cl.
*A61B 5/00* (2006.01)
*A61B 7/00* (2006.01)

(52) U.S. Cl.
CPC .......... *A61B 5/4803* (2013.01); *A61B 5/4082* (2013.01); *A61B 5/7275* (2013.01); *A61B 7/00* (2013.01)

(58) Field of Classification Search
USPC ........................................ 704/205–210, 270
See application file for complete search history.

(56) References Cited

U.S. PATENT DOCUMENTS

2004/0044273 A1    3/2004  Keith et al.
2009/0208913 A1*   8/2009  Xu ..................... A61B 5/7264
                                                          434/169

(Continued)

FOREIGN PATENT DOCUMENTS

KR    10-1182069      9/2012
WO    2006/109268    10/2006

OTHER PUBLICATIONS

International Search Report and the Written Opinion, mail date Jan. 24, 2014, PCT/ISA/220, PCT/ISA/210, PCT/ISA/237.

*Primary Examiner* — Abul Azad
(74) *Attorney, Agent, or Firm* — Saliwanchik, Lloyd & Eisenschenk

(57) ABSTRACT

Detection of neurological diseases such as Parkinson's disease can be accomplished through analyzing a subject's speech for acoustic measures based on human factor cepstral coefficients (HFCC). Upon receiving a speech sample from a subject, a signal analysis can be performed that includes identifying articulation range and articulation rate using HFCC and delta coefficients. A likelihood of Parkinson's (Continued)

disease, for example, can be determined based upon the identified articulation range and articulation rate of the speech.

19 Claims, 7 Drawing Sheets

(56) References Cited

U.S. PATENT DOCUMENTS

| | | |
|---|---|---|
| 2010/0174533 A1 | 7/2010 | Pakhomov |
| 2012/0265024 A1* | 10/2012 | Shrivastav ............... A61B 5/40 600/300 |
| 2015/0154980 A1* | 6/2015 | Khan ...................... G10L 25/66 704/203 |

* cited by examiner

SCREENING FOR NEUROLOGICAL DISEASE USING SPEECH ARTICULATION CHARACTERISTICS

CROSS-REFERENCE TO RELATED APPLICATIONS

This application is a national stage application of International Patent Application No. PCT/US2013/064041, filed Oct. 9, 2013, which claims the benefit of U.S. Provisional Patent Application No. 61/714,434, filed Oct. 16, 2012, both of which are incorporated herein by reference in their entireties.

BACKGROUND OF THE INVENTION

Traditionally, disease diagnosis relies on specific chemical biomarkers (such as proteins, antibodies, and cell types) and/or physiological changes (such as a change in body temperature or tissue color). These traditional tests tend to require active participation from the patient. For example, an at-risk individual often must voluntarily seek medical testing before a diagnosis can be rendered. Furthermore, these screening tests can be invasive in nature (e.g., requiring blood to be withdrawn), which further limit the acceptance or routine use of these tests. In addition to detectable chemical biomarkers and/or physiological changes, diseases also lead to functional or behavioral changes in a person. For example, some diseases may cause nausea, lethargy, cough, tremors, speech deficits, and disruption in sleep or feeding behavior. Therefore, in addition to research being conducted in methods for diagnosing various diseases, research continues to be conducted for finding effective methods for enabling and facilitating screening for diseases and other medical conditions.

BRIEF SUMMARY

The present disclosure is directed to screening for neurological and other diseases and medical states using speech behavior as a biomarker, and systems, applications, and methods for accomplishing the same.

In a particular embodiment, screening for a neurological disease, such as Parkinson's Disease (PD) can be accomplished using articulation characteristics of speech. In a specific embodiment, human factor cepstral coefficients can be used as a biomarker for detection of PD.

Embodiments of the invention can be implemented as a hardware and/or software package for physician, rehabilitation professional, or other medical professional use, or as a direct-to-consumer device.

In certain embodiments, the subject screening methods can be implemented as services or applications performed through telephony, cable, satellite, and/or the internet.

According to certain implementations, mass screening for infectious or other diseases, while requiring little or no active participation from the users, can be accomplished.

DETAILED DISCLOSURE

Figure 1:
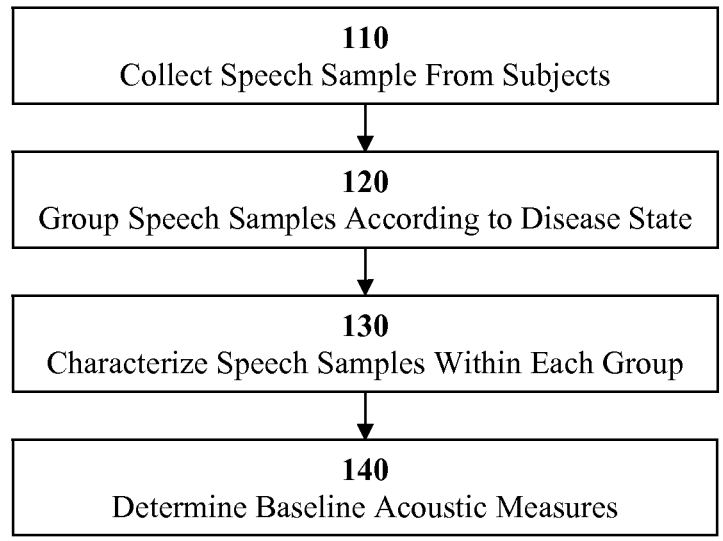
FIG. 1 shows a process flow diagram of a method for determining baseline acoustic measures in accordance with an embodiment.

Systems and methods of screening for neurological and other diseases and medical states utilizing a subject's speech behavior are provided.

In accordance with an embodiment of the invention, consistent diagnosis of neurological and other diseases can be accomplished through quantifiable measures of acoustic characteristics of a person's speech to determine what is being spoken or how it is being produced.

According to certain embodiments of the invention, speech and/or language changes can be used as biomarkers for neurological diseases. "Speech" refers to how something is being said, and "language" refers to what is being said. A person's speech can include other vocal behaviors such as cough or laugh.

These quantifiable measures of acoustic characteristics of a person's speech provide one or more biomarkers indicative of a likelihood of disease onset and/or stage of degeneration. The biomarkers may be determined, for example, from acoustic analyses of the speech signal, by the application of an automatic speech recognition system including large vocabulary systems, phoneme detection, word spotting engines or the like, and the application of syntactical coding or transcription on input speech. In some cases, an auditory processing model or some alternate non-linear transformation may be used to characterize a person's speech prior to computation of any input signal characteristics.

Some transformations, such as the use of an auditory-based front-end may allow transformation of acoustic (physical) parameters to corresponding psychoacoustic (psychological) parameters. For example, "frequency," measured in Hertz, is the number of cycles completed per second. The inverse of the frequency is the "period" of the signal, measured in seconds. Frequency and period are physical properties of a particular sound. On the other hand, "pitch" is a psychological attribute that is related to frequency and may be approximated using scales such as mels, barks or equivalent rectangular bandwidth distances (ERBs).

In general, the higher the frequency of a sound, the higher is its pitch. However, the relationship between frequency and pitch is not linear and pitch can be affected by factors other than frequency alone.

Similarly, "intensity," measured in watts/m$^2$, and "intensity level," measured in decibels, are physical measures of the energy or power of the signal. "Loudness," measured in Sones, is the psychological correlate of intensity.

In general, as the intensity increases so does its loudness. However, intensity and loudness are not identical, and just like pitch and frequency, the relationship between intensity and loudness is highly complex and non-linear.

The auditory processing models can allow computing of the loudness of a sound if the intensity level, frequency, and duration characteristics of the sound are known. However, the intensity level of the sound cannot be determined if only its loudness is known.

Systems and methods of screening for a neurological or other disease in a subject by the use of comparative analysis of speech behavior associated with the neurological or other disease to diagnose or predict the a likelihood of developing the neurological or other disease are provided.

In addition, similar systems are described using cough as an indication of disease.

Screening performed in accordance with certain embodiments of the invention includes diagnosing or predicting neurological and other diseases or medical states in a subject by analyzing speech behavior in samples from the subject. The screening may be carried out on a subject having a neurological or other disease, a subject at risk of having a neurological or other disease, or even a subject having no known risk of having a neurological or other disease.

A systematic, long-term evaluation of functional symptoms is rarely undertaken in clinical practice, yet these are the very symptoms that make a patient seek medical care. In one implementation of an embodiment of the invention, a long term evaluation of functional symptoms is achievable. In one embodiment, systems and methods are provided to systematically track functional symptoms over long periods of time and alert users before a disease becomes endemic and/or the functional symptoms become disruptive to an individual.

In certain embodiments, the speech and language of a speaker may be monitored over different periods, ranging from a few minutes to several days, weeks, months, or even years. During this monitoring, candidate biomarkers can be tracked to determine their presence/absence or the degree to which these change over time. These data can be compared to some normative database or to some specified criteria, and results of the comparison can be used to predict the likelihood of one or more neurological/neurodegenerative or other disease, such as infectious and/or respiratory disease, condition(s).

Certain embodiments of the invention are directed to passive screening. Screening is considered "passive" when a user does not need to actively do anything while being screened other than the user's normal activities. In one embodiment, mass passive screening can be accomplished where groups of people can be screened using the same or similar systems without their having to perform any active steps. The groups of people can be simultaneously screened using the same system. For example, for an embodiment where the screening is provided as a service through a telephony, internet, voice over IP (VoIP), or cell phone service provider, any user of the service provider can be screened and/or routed through a screening device.

The methods as provided herein can be used to diagnose or indicate a likelihood of developing a neurological or other disease in a subject, to detect specific conditions of a neurological or other disease in a subject, to monitor a change in a neurological or other disease in a subject, and/or to monitor effects of specific drugs, surgical treatments or rehabilitative efforts.

By using acoustic measures as a biomarker, a speech sample can be analyzed and a diagnosis or probability of disease can be provided to a patient or practitioner.

Using acoustic measures as a biomarker involves evaluating changes in various aspects (or subsystems of speech) over time. These subsystems include, but are not limited to, aspects such as articulation (i.e. the way in which various consonants and vowels are produced), the prosody or intonation (i.e. the tone of voice), the voice or vocal quality, overall speech intelligibility (i.e. how much of the message or meaning can be conveyed by the speaker under ideal or non-ideal conditions), the rate of speech and changes in the rate of speech across an utterance, etc. The analyses may also include, but is not limited to, analyses of the number of words spoken, the types of words (e.g. nouns, verbs, adjectives, articles, etc.) grammatical complexity of the phrases and/or sentence, the number of occurrence of specific words/phrases in conversation, or instances of dysfluencies such as pauses, hesitations or repetitions of words or part-words. The analysis may also evaluate, as an alternative or in addition, the frequency (i.e. the number of occurrences), the intensity (i.e. the strength), or other characteristics of cough during a conversation. Of course, embodiments are not limited to these listed, and other measures from a speech sample can be taken and analyzed.

According to laboratory tests conducted in accordance with an embodiment of the invention, it has been demonstrated that an expert listener can reliably differentiate the speech of normally aging men and women from the speech of those with Parkinson's disease (PD), including mild and only recently diagnosed forms of this condition. The paper entitled "Acoustic characteristics of Parkinsonian speech: a potential biomarker of early disease progression and treatment," by B. T. Harel et al. (Journal of Neurolinguistics, 17 (2004) pp 439-453), which is hereby incorporated by reference in its entirety, supports the assertion that speech has potential as a biomarker for disease. Additional testing conducted in accordance with an embodiment of the invention showed good results for being able to detect PD through a voice sample. According to the study, two experts were able to detect whether a voice sample belonged to a person who developed Parkinson's disease simply by listening to a single recorded sentence. In the test, 72-73% of PD and Normal samples were correctly classified by both experts. The tests were able to illustrate consistency (e.g., the two experts identified the samples similarly) and confirmed that speech has potential as a biomarker for disease.

Using these tests and other tests with experienced listeners, biomarkers in the speech associated with PD (or other diseases) can be determined and baseline acoustic measures can be created. For example, the baseline acoustic measures for the diseases can be created using a method including: collecting speech samples from patients at the time of their diagnosis; evaluating these samples using an expert listener naive to medical status of the patients corresponding to the speech samples; confirming accuracy of expert listener evaluations; conducting listening experiments to identify the salient perceptual characteristics in the speech; identifying critical acoustic correlates of the perceptual signs; providing the acoustic correlates to an analyzer tool; and reanalyzing the samples acoustically to guarantee similarity between the analyzer tool and the perceptual analysis of a human listener.

FIG. 1 is a flow chart illustrating a method of developing baseline acoustic measures associated with neurological or other diseases according to one embodiment of the present invention. A set of baseline acoustic measures associated with a neurological or other disease can be developed using speech behavior. The baseline acoustic measures can be obtained by first collecting speech samples from subjects (step 110). In developing such baseline acoustic measures associated with a neurological or other disease, speech samples from a variety of subjects known to be afflicted with a given neurological or other disease, as well as subjects known to be disease free can be gathered. The subjects known to be afflicted with a disease can be at a variety of stages of degeneration caused by the neurological or other disease and may also have samples obtained over time. The span of disease states associated with the samples can vary based on the disease being analyzed. A more rapidly degenerative disease can, for example, require a shorter span than a slower degenerative disease.

Next, in step 120, the speech samples can be grouped into sets based on how far along the disease has progressed. The sets can cover a predetermined period of time, for example, 3 month intervals. One step in the grouping process can be to establish the chronological boundaries of the participant's sample base. The samples can then be quantified and averaged. Depending on the implementation, extreme anomalies can be dismissed so that they do not unduly affect the process. The average of each feature can then be charted against time. For example, the average variability of a fundamental frequency ($F_0$) can be charted against time over the analysis period and compared against the variability of $F_0$ from a healthy group.

Next, in step 130, the speech samples can be characterized within each group. For example, trends in feature changes can be determined using acoustic measures and feature changes are correlated to determine whether the changes can be attributed to the neurological or other disease.

In step 140, baseline acoustic measures can be determined from the characterized speech samples. The baseline acoustic measures can be used in diagnostic tools using speech behavior as a biomarker of the onset of the neurological or other disease. In one embodiment, the baseline acoustic measures can be arranged and stored in the form of look-up tables or other organized storage format.

According to an embodiment of the invention, acoustic biomarkers can be recorded and a patient can be monitored over a period of time (such as a few days to several years). A comparison with look-up tables or a rapid change in specific biomarkers can indicate a greater likelihood of a disease.

In an embodiment of the invention, the output of the likelihood and type of disease state is stored in a database. Medical practitioners having access to the information may follow the prescribed treatment programs or augment them based on the individual needs of the subject. Subsequent diagnostic determinations are stored in a database and may be compared to previous diagnostic determinations to characterize a subject's adherence to a prescribed treatment plan. Information related to the likelihood and type of disease state may also provide an accurate determination regarding a change or progression in disease state.

In accordance with an embodiment of the invention, one or more acoustic measures for Parkinson's disease can include, but are not limited to, fundamental frequency ($F_0$), voice onset time, pause duration, and/or changes in $F_0$; voice onset time, and/or pause duration; fricative noise characteristics; stop burst duration; burst spectral characteristics; changes in speaking rate within or across phrases/sentence; changes in formant frequencies; and changes in formant frequency transitions. In addition, one or more acoustic measures for neurological and other diseases can include, but are not limited to, measures of aspiration noise, frequency and intensity perturbation; signal-to-noise (SNR) ratios; changes in pitch over time; changes in loudness over time; and/or other temporal and/or spectral characteristics of a speech sample(s). The one or more acoustic measures also can include a measure of partial loudness. In one embodiment, acoustic measures associated with neurological and other diseases can include a measure of low frequency periodic energy, a measure of high frequency aperiodic energy, and/or a measure of partial loudness of a periodic signal portion of the speech sample. The acoustic measure of the speech sample can further include a measure of noise in the speech sample and a measure of partial loudness of the speech sample. Of course, embodiments are not limited thereto. In one embodiment, the analysis can include evaluation of the frequency (i.e. the number of occurrences), the intensity (i.e. the strength) or other characteristics of cough during a conversation.

Similarly to PD, the biomarkers for Alzheimer's disease may include the measures described above as well as detailed analyses of the speaker's language characteristics. These may be determined through analyses of the number of words spoken, the types of words (e.g. nouns, verbs, adjectives, articles, etc.), grammatical complexity of the phrases and/or sentence, the number of occurrence of specific words/phrases in conversation, or instances of dysfluencies such as pauses, hesitations or repetitions of words or part-words. The analysis may also evaluate the frequency (i.e. the number of occurrences), the intensity (i.e. the strength) or other characteristics of cough during a conversation.

Biomarkers for respiratory diseases may include cough. A common symptom of many diseases, and particularly infections of the respiratory tract, is an increase in the number (frequency) and strength of cough. Therefore, the analysis for such disease or medical conditions includes evaluating the frequency, intensity, or other characteristics of cough during a conversation. In addition, unlike certain acute conditions (such as a cold or allergies), the cough resulting from infection disease typically lasts for longer durations. For example, tuberculosis can result in a cough lasting several weeks.

The biomarkers described above may be suitably weighted and combined using appropriate statistical, pattern-recognition and/or machine learning techniques prior to making a diagnostic decision. These include, but are not limited to, discriminant analyses, regression, hidden Markov-models, support-vector machines, and neural networks.

Figure 2A:
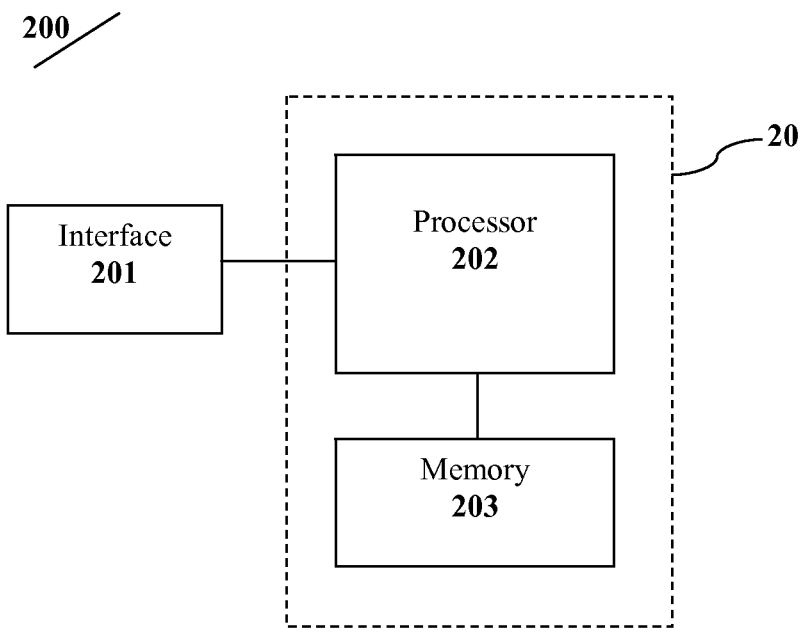
FIG. 2A shows a block diagram of an identification device according to an embodiment of the invention.
Figure 2B:
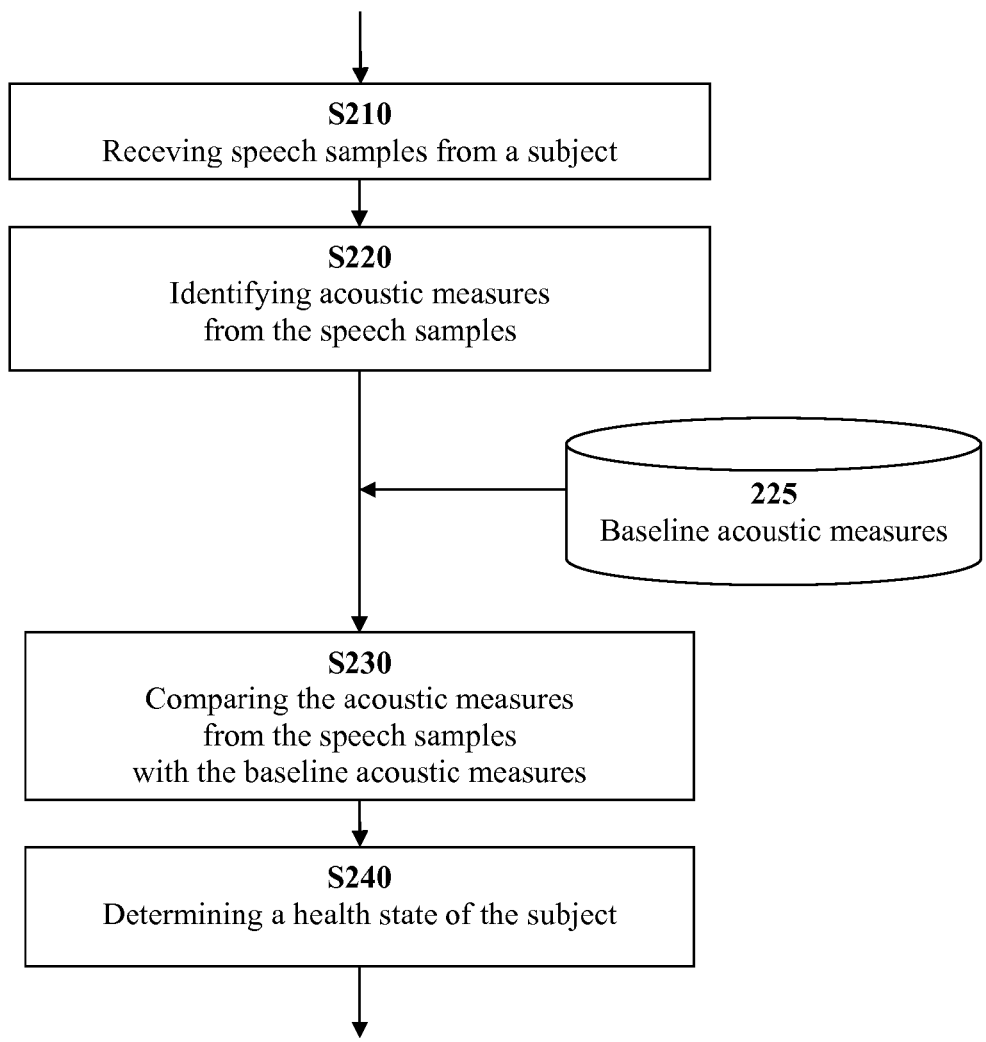
FIG. 2B shows a flowchart of a method of determining a health state of a subject using the identification device of FIG. 2A according to an embodiment of the invention.

The analytical tool using the stored baseline acoustic measures can be embodied in hardware, software, or a combination of hardware and software. Referring to FIG. 2A, an identification device 200 used as an analytical tool can include an interface 201, a processor 202, and a memory 203. FIG. 2B shows a flowchart of a method of determining a health state of a subject performed by the identification device 200.

According to an embodiment of the invention, baseline acoustic measures can be stored in the memory 203. The identification device 200 can be used to determine a health state of a subject by receiving, as input to the interface 201, one or more speech samples from a subject (S210 of FIG. 2B). The interface 201 then communicates the one or more speech samples to the processor 202, which identifies the acoustic measures from the speech samples (S220 of FIG. 2B) and compares the acoustic measures of the speech samples with the baseline acoustic measures 225 stored in the memory 203 (S230 of FIG. 2B). The processor 202 can determine a health state of the subject based upon the results of the comparison or by tracking the rate of change in specific baseline acoustic measures (S240 of FIG. 2B). The processor 202 can then output a diagnosis. The diagnosis can be obtained by a user through the interface 201. The results may be provided via phone, email, text messaging, mail, an attached or networked printer, website interface, or directly on a display screen of the device.

Embodiments of the invention can be implemented as a hardware and/or software package for physician, rehabilitation professional, or other medical professional use, or as a direct-to-consumer device.

In one embodiment, the identification device 200 can be located at the testing site of a patient. In one such embodiment, the identification device 200 can be part of a computer or mobile device such as a smartphone. The interface 201 can include a user interface such as a graphical user interface (GUI) provided on a screen or display. An input to the identification device 200 can include a microphone, which is connected to the device in such a manner that a speech sample can be recorded into the device 200. Alternately, a speech sample can be recorded on another medium and copied (or otherwise transmitted) to the device 200. Once the speech sample is input to the device 200, the processor of the computer or mobile device can provide the processor 202 of the device 200 and perform the identification procedures to determine the health state of the subject. The results of the determination can be provided through the interface 201 onto the screen or display of the computer or mobile device.

In a specific embodiment utilizing a smartphone, an application (app) on the phone can be accessed and, when selected to run, the app brings up a GUI providing the interface 201 on the screen of the phone. In an embodiment, a speech sample can be recorded by the phone through the phone's microphone. The screening app on the phone may prompt the user to record a sample of their speech and/or request a sample already stored in the phone's memory, which may provide the memory 203 of the identification device 200 when the screening app and baseline acoustic measures are stored entirely on the phone. The screening app can perform the steps to determine the health state of the subject. In a further embodiment, the results from the screening can be transmitted to a healthcare provider.

Figure 3:
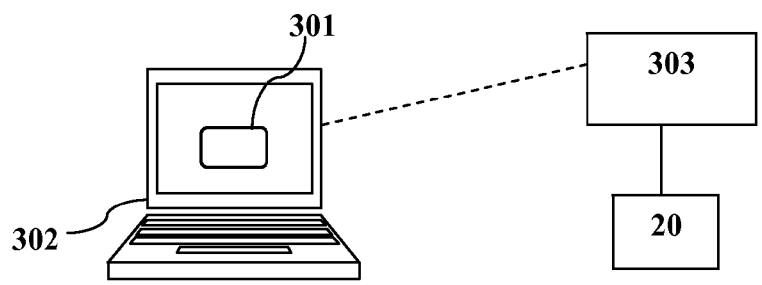
FIG. 3 shows a system configuration according to an embodiment of the invention.

In one embodiment, the system package can be of two parts, such as shown in FIG. 3. One part is to be located at an end user office, such as at a clinic, rehabilitation center, hospital, or home. The part at the end user office can include hardware and/or software. In one embodiment, a microphone can be part of the hardware. Recording equipment and/or storage media may also be included. The software that may be included can provide a user interface 301 when provided at a terminal 302 (such as a computer). The second part of the system package remains at a central server 303, which can include the analyzer module 20 of the identification device 200 (see also FIG. 2A), and provides the analysis of the speech samples as well as storing the baseline acoustic measures.

For a physician or other medical professional-based system, when the physician or medical professional wants a patient to perform a test, the physician or medical professional has the patient register a speech sample with the device. For a direct-to-user system, a person can register a speech sample with the device as and when needed. The analysis of the speech sample occurs at the central server and the results are provided to the physician and/or the patient. This arrangement can be referred to as a client-server model.

In another embodiment, telephony services are utilized to provide a direct-to-consumer screening program. In one embodiment for telephony services, a consumer can enroll in a screening program. The screening program can provide passive screening for the neurological or other diseases. By enrolling in the program, the consumer consents to having phone calls monitored. In one embodiment, the monitoring occurs within the phone network by having the consumer's voice characterized according to acoustic measures as the consumer's conversations are passed through the phone network's servers. In another embodiment, calls are passed through to an outside server and characterized at the outside server before rerouting to the recipient of the phone call of the consumer. The outside server may be through an application service provider (ASP). It should be understood that the conversations are not necessarily being monitored; rather, the speech signals are analyzed according to identified acoustic measures of the waveform. Furthermore, in one embodiment, the consumer can have the ability to temporarily disable the passive screening program, such as through a website or by dialing a specific access code on their telephony service. In another embodiment of the invention, the user can have a notification transmitted to them-self as a reminder to the user to provide the speech sample at a regularly scheduled interval. The user may produce speech samples that correspond to a scheduled time, day, week, or month that repeats at a predetermined frequency. Further analysis of the speech samples can be provided based on potential changes in the speech samples taken at the specified intervals. If speech parameters of the consumer indicate a certain probability of disease, the consumer can be warned. The warning can be in the form of a phone call, and email, a text, or other form of communication. Optionally, the consumer can be prompted to complete a more specific test on the phone. Based on the test results, the consumer is directed for further action. The further action may include scheduling an appointment with a doctor and/or a rehabilitation program.

In yet another embodiment, internet services are utilized to provide a direct-to-consumer screening program. In one embodiment for internet services, a consumer can enroll in a screening program via a website. The screening program may require the consumer to regularly or periodically register a speech sample. The speech sample is uploaded to a server through a network connected to the terminal used by the consumer. The website provides the interface 201 of the identification device 200. According to certain embodiments, the website can be accessed by any terminal connected to a network through an internet service provider.

The registration of the speech sample can be prompted by reminders to the consumer sent for example by phone, email, or text. The program can require monthly (or other time frame) registration. If speech parameters indicate higher probability of disease, the consumer is suitably warned and additional tests/follow-up recommended.

Figure 4:
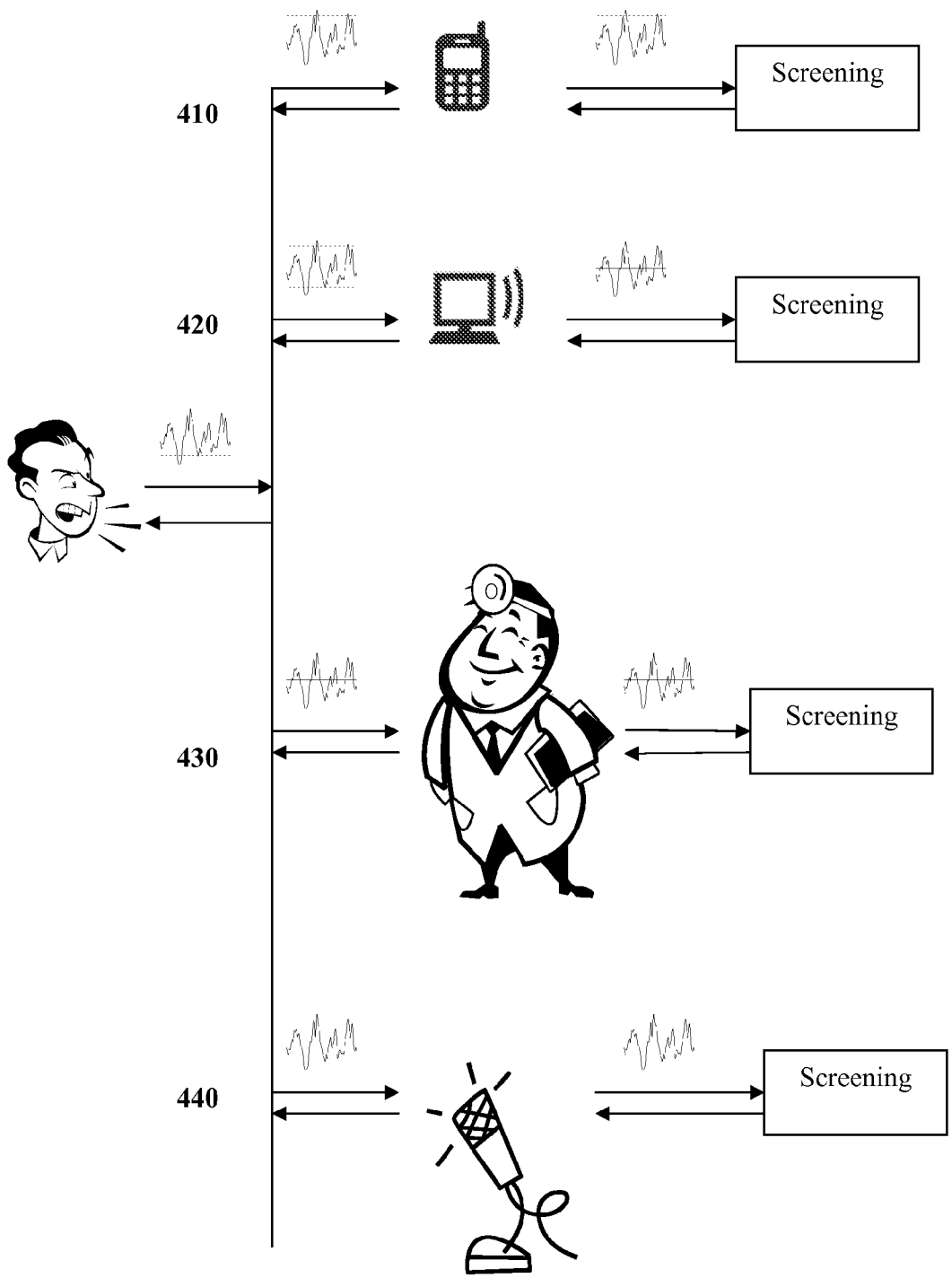
FIG. 4 shows a flowchart of a screening method according to an embodiment of the invention.

FIG. 4 illustrates some examples of screening models that can be implemented in accordance with embodiments of the invention.

For a telephony-based model 410, a subject can provide a speech sample (intentionally or passively) through a telephone service provider to be screened. Results of the screening or instructions for further action may be provided to the subject by phone, email, text, etc., either immediately upon a diagnosis or determination of a high likelihood of developing the disease or at a later date. In one embodiment, the subject may be asked to complete a more specific test on the phone to allow for a rechecking or confirming of the diagnosis. Screening can continue after diagnosis to monitor whether additional degradation occurs.

For an internet-based model, 420, speech samples are uploaded regularly by a subject for screening. The subject can be reminded to upload the speech samples in order to test for the biomarkers at regular or periodic intervals. Results of the screening or instructions for further action may be provided to the subject through a website, phone, email, text, etc.

For a physician-based model 430, speech samples from a subject are obtained at a clinic or hospital, and a physician or assistant supplies the speech samples to be screened. The identification device for determining the health state of the patient can follow the client-server model, or be part of a piece of equipment at the clinic or hospital. After the identification device completes the analyses of the speech samples through the device at a clinic or hospital, the results are provided to the physician and the patient.

For a direct device-based model 440, a subject registers a speech sample as and when needed. The device can be client-server based or as a self-contained hardware and/or software package. Once the analysis is performed on the speech sample, the customer can receive a report including results and further recommended action, which may be generated from the device. The direct device model can be implemented, for example, similarly to blood pressure machines found in drug stores and other public locations.

A patient may take advantage of one or more of such models and/or select the model most appropriate for the patient's needs and monitoring requirements.

According to certain embodiments, after an initial screening indicating diagnosis or high likelihood probability of a disease, the subject programs can provide continued monitoring of the disease states and adjustments to directions of further action.

Figure 5:
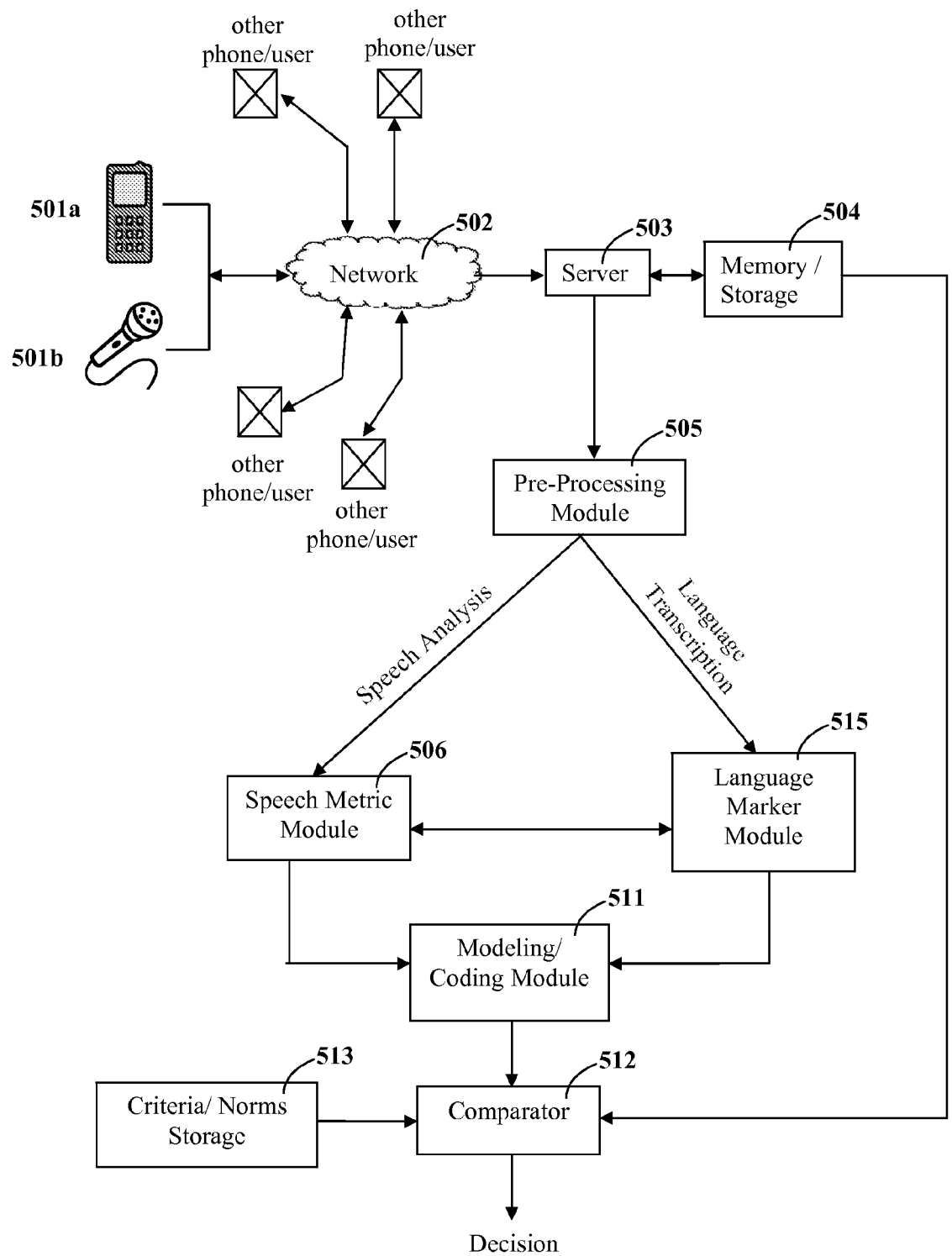
FIG. 5 shows a diagram of a screening system according to an embodiment of the invention.

FIG. 5 illustrates a screening system according to an embodiment of the invention. The screening system shown in FIG. 5 is applicable to the identification device and system packages described with respect to FIGS. 2-3. Referring to FIG. 5, a person's voice is input through a telephone or mobile communication device 501*a* or microphone 501*b* and transmitted to a server 503, such as an ASP, via a network 502. The voice signal can be transmitted via internet, phone, VoIP, satellite, cable, cellular or other networks. Accordingly, mass screening can be accomplished for users of the network provider. The server 503 may include a database, memory or other storage device 504 that can retain previous voice samples of the same user, voice samples of other users connected to the network, and/or data related to the user(s). Accordingly, it is possible to obtain, analyze and monitor biomarkers in speech/language over long periods of time.

Once the voice sample is provided to the server 503 via the network 502 or service provider, pre-processing can be performed to remove noise and other elements from the voice sample. For cellular networks, the processing modules of certain embodiments of the invention can be easily scaled for any cellular network regardless of specific mobile phone technology (e.g. CDMA/GSM, different types of vocoders, types of handsets). In other embodiments, the processing modules can be calibrated to account for differences in mobile phone technology across carriers. The pre-processing module 505 can evaluate the condition of the signal and perform signal conditioning. The signal conditioning can include, but is not limited to, removing contaminated segments and/or filtering the signal. The pre-processing module 505 can reduce noise in the signal. In one embodiment, the pre-processing module 505 can be used to select speech segments for further analysis. In a further embodiment, after performing the pre-processing, an auditory-based or other non-linear transformation, such as a logarithmic transformation, can be applied as a front end for signal processing before the signal is analyzed.

In one embodiment using a passive screening model a microphone/recording system can be located at a home, nursing home, hospital, long-term care facility, work place or other location for passive recording of data from a user. The collected data can be uploaded to the server 503 for further analysis either by an automatic upload or by intentional request by a practitioner or user. In such an embodiment, the pre-processing module can include algorithms to determine the speaker identity and algorithms to isolate the speech of one speaker from another.

During the analysis stage, the user's speech and/or language can be analyzed. The system can include one or both analysis capabilities.

For speech analysis, the user's speech is analyzed according to predetermined metrics (acoustic measures) in a speech metrics module 506. For example, acoustic analysis can be performed to quantify metrics including, but not limited to fundamental frequency characteristics, intensity, articulatory characteristics, speech/voice quality, prosodic characteristics, and speaking rate.

Figure 7:
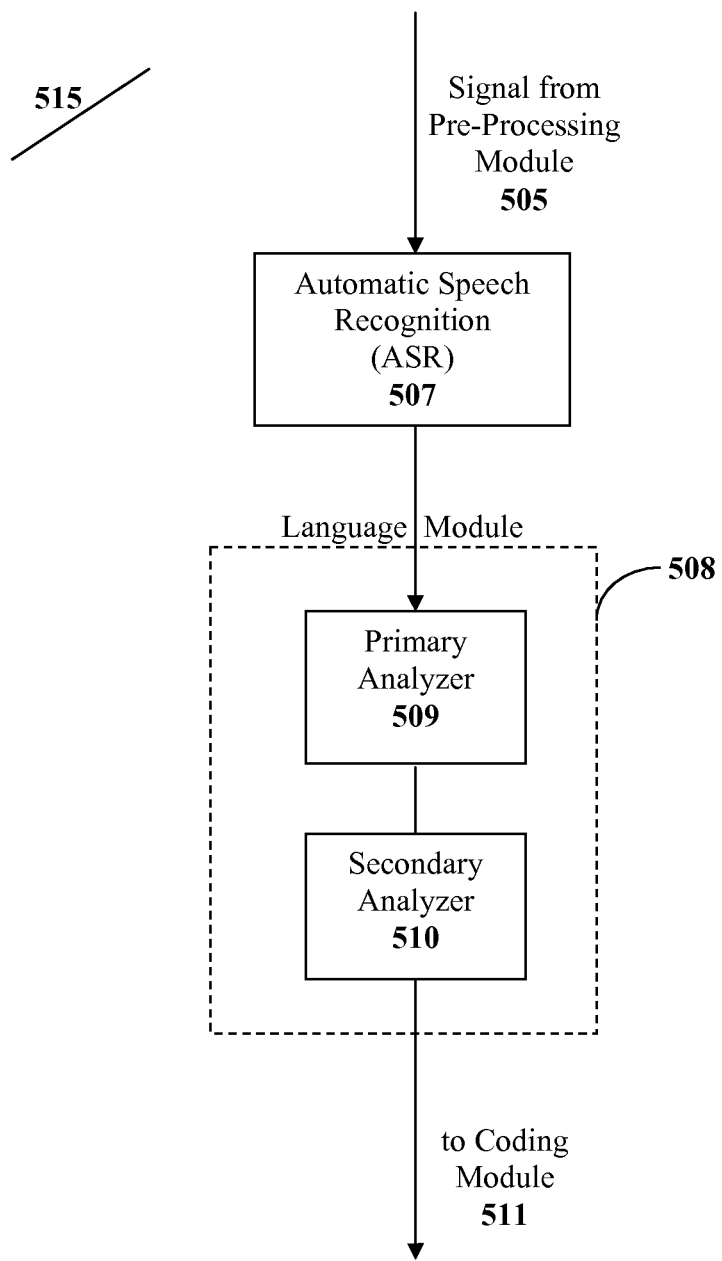
FIG. 7 shows a diagram of a portion of the screening system according to an embodiment of the invention including a language marker module.

For language analysis, the user's language is analyzed for language patterns in a language marker module 515. The language marker module 515 can include an automatic speech recognition (ASR) module 507 and a language module 508. As shown in FIG. 7, according to one embodiment, the user's language is transcripted via the ASR module 507, which can incorporate large vocabulary systems, word spotting, and phoneme recognition. Then, once the words (language) are determined by ASR, recognized words (and phrases and sentences) can be classified into syntactical categories in the language module 508. For example, recognized words can be classified as nouns, verbs, and adjectives. Then, phrase and/or sentence complexity can be determined by, for example, evaluating the number and order of various syntactical categories that occur in someone's speech. In one embodiment, a primary analysis 509 for syntax coding can be performed to classify the recognized words/language. The syntax coding can be accomplished by a dictionary look-up. A secondary analysis 510 for sentence/phrase complexity can be performed to determine the complexity and usage of the language. A reduction in sentence complexity can be an indicator of a neurological disease. In addition, certain neurological diseases, such as Alzheimer's, cause particular language patterns to emerge. Such language patterns can be determined via the secondary analysis.

In certain embodiments having both speech and language analysis capabilities, the ASR module 507 and the language module 508 are interconnected with the speech metrics module 506. The outputs of the ASR module 507 and/or the language module 508 can be sent to the speech metrics module 506 for speech analysis of a particular output of the ASR or language module. For example, in order to analyze and track certain acoustic properties of a very specific vowel or consonant (such as how long the speaker takes to make the sound "sss" in the word "slip"), the particular word (e.g. "slip") is scanned in the ASR module output. Once the word is found, the segment of the signal containing that word can be sent to the speech metric module in order to calculate particular acoustic properties, such as the duration of the "ssss" sound.

After performing the speech and/or language analysis, modeling and coding can be performed by the coding module 511 via statistical approaches, machine learning, pattern recognition, or other algorithms to combine information from various biomarkers before reaching a diagnostic decision.

Once the information from the speech and/or language analysis is obtained, comparators 512 can be used to reach a diagnostic decision. For example, in one embodiment, the biomarker information of the signal is compared to a normative data set (norm-based test), such as the baseline acoustic measures stored in a memory or other storage device 513 connected with the comparator or average measures obtained from other users of the system that may be stored in the memory or other storage device 504 connected with the server. In another embodiment, the biomarker information of the signal is compared to a set of rules (criterion-based test), which may be stored in the memory or other storage device 513. In yet another embodiment, the biomarker information of the signal is compared to previous biomarker information from the user to compare changes in biomarkers over time. In such an embodiment, trajectories may be estimated or rate-of-change can be determined. In certain embodiments, one or more of these comparisons can be performed. The diagnostic decision is then output by the comparator 512. The diagnostic decision provides information indicative of a likelihood and type of disease and may be stored in a database associated with the system.

In an embodiment of the invention, the user's speech information from the speech analysis is sent directly to the comparator 512 without the step of modeling and coding being performed by the coding module 511.

According to a further embodiment, upon diagnosis of a disease or a likelihood of the disease, a rehabilitation program can be implemented. In certain embodiments, the rehabilitation program can be delivered and monitored remotely. For example, a patient can opt to enroll in rehabilitation, and a set of exercises can be recommended over the telephone/internet based upon the diagnosis or prognosis. In addition, the patient's completion of exercises, performance results, etc. can be monitored through the same channels. The subject devices and systems can be used to continue to monitor and screen a patient over time.

The monitoring of disease biomarkers in speech can detect individuals in very early stages of disease, thereby allowing early intervention. This aspect of certain embodiments of the invention enables reducing the severity of the disease for the affected individual (e.g., by early treatment), as well as minimizing of the spread of disease within a population.

One common symptom of respiratory tract infections, including tuberculosis and influenza, is coughing. The exact nature and duration of the cough can vary from one disease to another, but the intensity (strength), frequency (number of occurrences) and the duration for which a cough lasts (time since onset) are variables that can help identify infectious disease and differentiate an individual with an infectious disease from non-infectious conditions. For example, unlike certain acute conditions (such as allergies), the cough resulting from infectious diseases typically lasts for longer durations. Some conditions, such as tuberculosis, result in cough lasting several weeks.

In addition, one marker of airway infections is a change in voice quality resulting from factors such as laryngeal inflammation or upper airway obstruction. In certain embodiments, by combining information about cough behavior with speech (for example, change in voice quality), the likelihood of a particular disease can be determined. As used herein, "voice quality" can be defined as all characteristics of voice production that differentiates speakers producing the same sound, phonemes, or syllables (e.g. same vowel and/or consonants) despite having the same (or equal) fundamental frequency and loudness. It should be understood that "voice quality" is being distinguished from "speech intelligibility," which refers to how much meaning/information can be understood from speech. For example, speech may have poor "quality" but good "intelligibility"—meaning a person's intent can be easily understood, even though they may be talking with a hoarse voice or whisper.

In further embodiments, information obtained related to cough behavior and changes in voice quality can then be combined with other information and data such as meteorological information (e.g. temperature and humidity), incidence of diseases in the population, the speaker's age, gender, ethnic/racial background, socio-economic status, predisposition to specific diseases, and geographical or location information (e.g., location and address), etc., to further improve the accuracy of screening for infectious diseases and/or determine a likelihood of a particular disease. The other information or data may be obtained through various sources and either stored in a local database or accessed as needed. Furthermore the combination of such information from a variety of sources (and at different locations) can enable modeling of disease incidence, spread of disease and determination of endemic or epidemic nature of specific diseases.

For example, an individual who presents a strong cough consistently for three or more weeks has a relatively high likelihood of suffering from tuberculosis. Groups of people residing in close proximity (household, neighborhood, etc.) and exhibiting similar changes at the same time would indicate the infectious nature of disease. Monitoring mobile phone speech/cough patterns of entire populations (neighborhood, villages, etc.) can allow early detection of diseases and allow public-health officials to take the necessary steps to prevent further escalation. In certain embodiments, information can be relayed to individual users urging them to seek medical care.

In accordance with certain embodiments of the invention, a screening system is provided that can monitor for a respiratory disease. In one embodiment, a similar system as described with respect to FIG. 5 can be used, where the screening for respiratory diseases can be accomplished by using cough as a biomarker. For example, referring to the system illustrated in FIG. 5, once the voice sample is provided to the server 503 via the network 502 or service provider, pre-processing can be performed to remove noise and other elements from the voice sample. The pre-processing module 505 can evaluate the condition of the signal and perform signal conditioning. The signal conditioning can include removing contaminated segments and/or filtering the signal. The pre-processing module 505 can reduce noise in the signal. In one embodiment, the pre-processing module 505 can be used to select speech segments for further analysis. These segments can be referred to as "windows."

In a further embodiment, after performing the pre-processing, an auditory-based or other non-linear transformation, such as a logarithmic transformation, can be applied as a front end for signal processing before the signal is analyzed.

A metrics module can receive the window of the audio stream and analyze the user's speech in the window according to predetermined metrics (acoustic measures). For the respiratory diseases, cough can be found and analyzed. This may be accomplished via an automatic speech recognition based analysis. In further embodiments, the acoustic analysis can be performed to quantify metrics including, but not limited to fundamental frequency characteristics, intensity, articulatory characteristics, speech/voice quality, prosodic characteristics, and speaking rate.

After performing the speech analysis, modeling and coding (511) may optionally be performed via statistical approaches, machine learning, pattern recognition, or other algorithms to combine information from various biomarkers before reaching a diagnostic decision.

Once the information from the speech/cough analysis is obtained, comparators 512 can be used to reach a diagnostic decision. The decision provides information indicative of a likelihood and type of disease. A base line of cough data for respiratory-type infections can be created by obtaining cough samples from a variety of sources, including hospital patients, clinic patients, and public databases (e.g., file sharing video and audio sites), evaluating the cough behaviors from the cough samples to develop the decision engine where speech samples of healthy individuals can be separated from people with respiratory-type infections, such as an upper airway infectious disease.

According to one embodiment, an audio (conversational) stream received via a phone/microphone (e.g., mobile phone, VoIP, internet, etc.) is analyzed by segmenting the audio stream into short windows, computing specific acoustic measures from each window (e.g. mel-frequency cepstral coefficients, human factor cepstral coefficients), comparing the acoustic measures across successive windows, developing and training a machine learning pattern recognition engine to identify acoustic patterns of a cough, and determining the likelihood of a particular window (or set of windows) to contain an instance of cough. In one embodiment, cough can be detected in an audio stream by applying signal analysis such as described by Stevens in "Toward a model for lexical access based on acoustic landmarks and distinctive features," (*J. Acoust. Soc. Am.* 111(4), 2002), which is incorporated by reference in its entirety.

Once cough is detected in the audio stream, the frequency, intensity, or other characteristics of the cough signals can be used to distinguish between diseases. For example, some conditions may result in a 'wet' cough characterized by a gurgly voice quality and others may be characterized by a 'dry' cough characterized by a hard onset (rapid attack time) followed by aperiodic (noise) energy.

The cough behavior of an individual can be tracked over a long period of time to determine how the cough changes over time. A rapid change in cough behavior or an escalation that is maintained over a prolonged period of time may indicate specific disease conditions.

In one implementation, a low-cost mobile phone based application is provided for monitoring health conditions. In one such implementation, individual users do not need any specialized equipment other than a standard mobile phone. The high penetration rate of mobile phones worldwide allows tests over the cellular and other networks to be deployed very easily for large populations. For example, specific infectious diseases are detected through monitoring and analysis of cough and conversational speech occurring over a mobile phone. This approach will allow mass screening for some infectious diseases, while requiring little or no active participation from the users. The passive nature of this approach makes it possible to have a very high penetration or acceptance rate that may, in some cases, be limited only by the number of mobile phone subscribers. In addition, tests can be administered to very large populations with little effort. The only disease biomarker needed from the users is a sample of their speech, which can be monitored automatically as people go about their routine conversations in daily life.

Furthermore, since the analysis is based on the speech of the phone user, the mobile phone itself does not require significant processing power or smart phone capabilities. Instead, in certain embodiments, the processing power can be embedded within (or distributed over) the network.

The incidence and type of cough behavior and voice quality can be monitored by monitoring mobile phone users' conversations over extended periods of time. According to an embodiment, signal processing algorithms are used to identify cough and voice quality within an audio (speech) stream. A pre-processing of the audio streams can be performed to reduce distortions caused by the mobile network or the vocoder of the phone. Data mining and decision engine or machine learning algorithms can be applied to provide diagnosis results.

By providing an early detection for neurological or other diseases, treatments can be provided that may slow or reverse the disease's progress. For example, emerging evidence suggests that exercise can be neuroprotective. Accordingly, certain further embodiments of the invention provide a series of exercises for one or more of the key components of the speaking mechanism, such as the respiratory system, larynx, velopharynx, and orofacial systems, as well as exercises for limbs and/or for balance. These exercises can be adapted to a neuroprotective program either alone or in combination with whole body exercise. The exercises may be constructed according to modern neuroplasticity and exercise principles.

Figure 6:
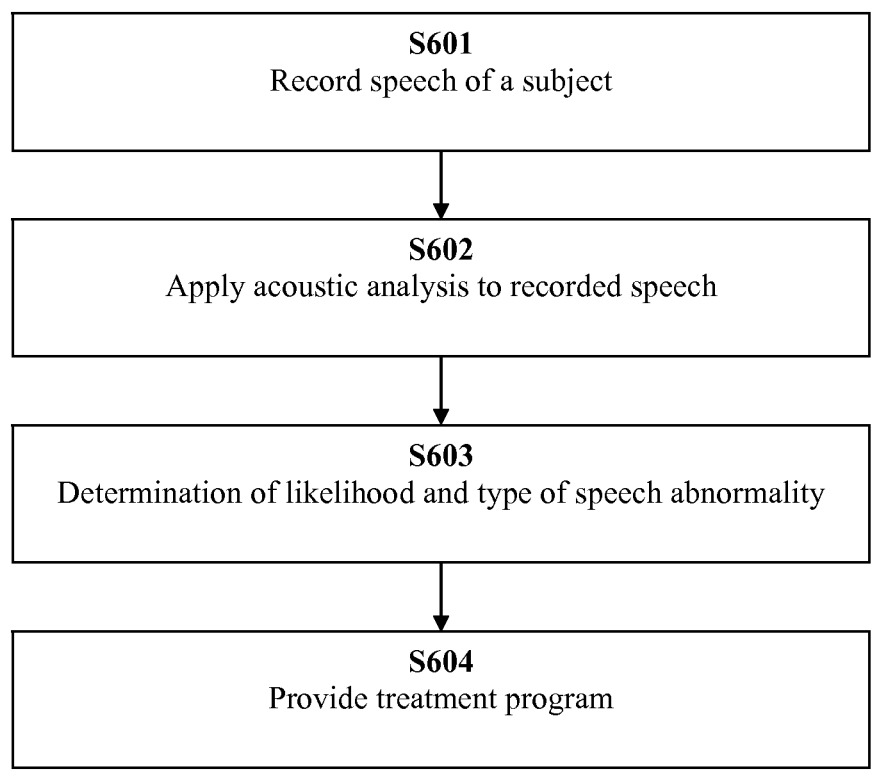
FIG. 6 illustrates services available for the screening of a subject in accordance with certain embodiments of the invention.

Thus, certain embodiments of the invention provide an identification and neuroprotective treatment package. The identification portion can be accomplished using one or more of the identification methods described herein. As one example, as shown in FIG. 6, a practitioner can make a brief recording of the speech (according to a protocol) of a patient using the identification and neuroprotective treatment package (S601). The patient may suspect something is wrong with an aspect of the patient's speaking and request the recording, or the practitioner may be suspicious about the patient's speech or general neurological status. Each sample (the recording of the speech for a period of time) can be subjected to acoustic analysis (S602). In one embodiment, the sample(s) can be uploaded to a server providing the acoustic analysis (e.g., client-server model). For example, a website may be provided with an interface allowing the practitioner to log in and upload samples. Once the sample is subjected to the acoustic analysis, a determination of the likelihood and type of speech abnormality (S603) can be provided to the practitioner. In addition, the practitioner (or patient) can receive a treatment program complete with instructions about how to perform each exercise, the schedule of exercising, and guidance about how to gauge success and when and how to modify the program (S604). The identification aspect of the package, which may indicate a medical diagnosis, can be confirmed by an appropriate specialist before the practitioner has the patient begin the treatment program.

Advantageously, by utilizing speech analysis, embodiments provide easy means of data collection as compared to more traditional evaluations of sensation, movement and balance, and provide a quantifiable analysis of results. By quantifying the results through the subject identification processes, a numerical likelihood of disease can be established, which shows improvement over perceptual judgments—even by an experienced listener.

The subject systems can be used to monitor therapy. In one embodiment a subject's adherence and performance on a particular treatment/rehabilitation program can be monitored via continued use of the subject systems. In addition, the change in disease status or progression of disease can be monitored once the subject is enrolled in the treatment/rehabilitation program.

For example, a patient with PD may be asked to speak with a greater intensity or with a slower rate of speech as part of the treatment/rehabilitation program. The subject screening systems can be used to monitor the patient's adherence to the program recommendations (such as the speaking at greater intensity or slower rate). Feedback can be provided as to whether the recommendations are being followed and/or whether the recommendations are, in fact, improving problems or slowing progression of the disease. In addition, monitoring speech/language changes over periods of time can help determine whether or not a particular treatment (drugs/rehabilitation exercise) is slowing down the progression of the disease.

Certain embodiments of the invention contemplate the use of a machine in the form of a computer system within which a set of instructions, when executed, may cause the machine to perform any one or more of the methodologies discussed above. In some embodiments, the machine can operate as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine can comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure can include broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The computer system can include a processor (e.g., a central processing unit (CPU), a graphics processing unit (GPU), or both), a main memory, and a static memory, which communicate with each other via a bus. The computer system can further include a video display unit (e.g., a liquid crystal display or LCD, a flat panel, a solid state display, or a cathode ray tube or CRT). The computer system can include an input device (e.g., a keyboard or keypad), a cursor control device (e.g., a mouse), a mass storage medium, a signal generation device (e.g., a speaker or remote control) and a network interface device.

The mass storage medium can include a computer-readable storage medium on which is stored one or more sets of instructions (e.g., software) embodying any one or more of the methodologies or functions described herein, including those methods illustrated above. The computer-readable storage medium can be an electromechanical medium such as a common disk drive, or a mass storage medium with no moving parts such as Flash or other non-volatile memories. The instructions can also reside, completely or at least partially, within the main memory, the static memory, and/or within the processor during execution thereof by the computer system. The main memory and the processor also may constitute computer-readable storage media. In an embodiment, non-transitory media are used. However, it should be understood that "computer-readable storage media" do not include propagating signals or carrier waves.

Dedicated hardware implementations including, but not limited to, application specific integrated circuits, programmable logic arrays, and other hardware devices, can be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, certain methods described herein are intended for operation as software programs running on one or more computer processors. Furthermore, software implementations including, but not limited to, distributed processing, component/object distributed processing, parallel processing, and virtual machine processing, can also be constructed to implement the methods described herein.

The present disclosure also contemplates a machine- (or computer-) readable medium containing instructions for executing particular tasks, and which may be a single medium or multiple media (e.g., a centralized or distributed database, and/or associated caches and servers) that stores the instructions. In an embodiment, non-transitory media are used.

Although the present specification describes components and functions implemented in certain embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

Aspects of the invention can be described in the general context of computer-executable instructions, such as program modules, being executed by a computer. Generally, program modules include routines, programs, objects, components, data structures, etc., that perform particular tasks or implement particular abstract data types. Such program modules can be implemented with hardware components, software components, or a combination thereof. Moreover, those skilled in the art will appreciate that the invention can be practiced with a variety of computer-system configurations, including multiprocessor systems, microprocessor-based or programmable-consumer electronics, minicomputers, mainframe computers, and the like. Any number of computer-systems and computer networks are acceptable for use with the present invention.

Certain embodiments of the invention can be practiced in distributed-computing environments where tasks are performed by remote-processing devices that are linked through a communications network or other communication medium. In a distributed-computing environment, program modules can be located in both local and remote computer-storage media including memory storage devices. The computer-useable instructions form an interface to allow a computer to react according to a source of input. The instructions cooperate with other code segments or modules to initiate a variety of tasks in response to data received in conjunction with the source of the received data.

Certain embodiments of the invention can be practiced in a network environment such as a communications network. Such networks are widely used to connect various types of network elements, such as routers, servers, and gateways. Further, the invention can be practiced in a multi-network environment having various connected public and/or private networks. Communication between network elements can be wireless or wired. As will be appreciated by those skilled in the art, communication networks can take several different forms and can use several different communication protocols.

Example 1

Acoustic Detection of Parkinson's Disease Using Human Factor Cepstral Coefficients Articulation is a detectable speech factor affected by neurological and other diseases, for example, PD. The expression of articulation errors in a diseased state reflect the mechanisms associated with articulation and the degree of coordination and control required for normal articulation.

In an embodiment of the present invention, articulation characteristics are measured using the standard deviation sum of cepstral coefficients and delta coefficients extracted from speech. In accordance with embodiments of the invention, human factor cepstral coefficients (HFCC), which are a variation of mel frequency cepstral coefficients (MFCCs), are used to represent the acoustics of the vocal track. Based on the correlation between the speaker's disease state and its effect on these parameters, the likelihood of the speaker having or developing a disease can be determined. In addition, these parameters may be used to monitor disease progression, efficacy of treatment, and/or need for changes in treatment.

Embodiments using HFCC as an acoustic measure are shown to be effective at predicting PD in talkers within a speech segment of short duration—such as for example a sentence. In certain embodiments, the HFCC acoustic measure described herein can operate on read speech as short as 2 seconds in duration. However embodiments are limited thereto and the speech samples may be of shorter or longer duration. The measure was designed to be a robust algorithm that does not require boundary detection (phonemes, syllables, words, or voiced-unvoiced-silence boundaries) and does not require phonetic analysis.

Articulation measures from read or spontaneous speech may be used for identification of a disease stage. Since articulation involves more degrees of freedom than steady-state phonation, articulation errors, independently or in conjugation with voicing errors, may allow for accurate detection of a disease based on acoustics of a subject. Further, articulation errors due to a disease may be more specific than alternations to the steady-state phonation signal, producing a detector of higher specificity. For example, PD may affect articulation in specific ways that allow for detection of PD based on acoustic parameters of a subject.

According to an embodiment, a speaker can be screened for PD by receiving a voice sample (either spontaneous, read, or previously recorded); applying an HFCC algorithm to frames of the voice sample to obtain an acoustic measure of the speaker; and comparing the speaker's acoustic measure to baseline values. Additional measures may be used in combination with the HFCC algorithm to obtain higher probabilities.

According to an embodiment, the HFCC algorithm can involve calculating the cepstral coefficient measure as follows:

$$\mu_i(k) = \frac{1}{L_i} \sum_{l=1}^{L_i} cc_i(k, l)$$

$$\sigma_i(k) = \sqrt{\frac{1}{L_i - 1} \sum_{l=1}^{L_i} (cc_i(k, l) - \mu_i(k))^2}$$

$$m_i = \sum_{k=1}^{K} \sigma_i(k)$$

where $cc_i(k,l)$ is the kth of K cepstral coefficients in the lth of $L_i$ frames for a voice sample i (e.g., a WAV file), $\mu_i(k)$ and $\sigma_i(k)$ are the mean and standard deviation, respectively, of the kth cepstral coefficient across frames, and $m_i$ is the scalar measure for the voice sample i. The delta coefficient measure can be obtained by replacing $cc_i(k,l)$ with $\Delta cc_i(k,l)$.

To illustrate an acoustic articulation measure sensitive to a disease, for example PD, an acoustic detection experiment was performed using "read sentence data" from normal and PD talkers. By using a difference in speaking rate and articulation precision between PD talkers and those with normal speech, an automated acoustic measure sensitive to articulation range and rate can be used to detect and track likelihood PD.

As shown by the experimental study, HFCCs can successfully be used to represent acoustics of the vocal tract and distinguish "normal" speakers from those with PD. For the experimental study, 78 talkers were tested with a total of 38 talkers pre-diagnosed with PD and 38 age-matched "normal" talkers. Each talker spoke 10 sentences selected randomly from a group of 16 high-predictability sentences taken from the Speech Perception In Noise Test specified by D. N. Kalikow et al. in their paper entitled "Development of a test of speech intelligibility in noise using sentence materials with controlled word predictability," (*J. Acoust. Soc. Am.*, vol. 61, no. 5, pp. 1337-1351, May 1977). The sentences were spoken one at a time and recorded continuously, including pauses between sentences. Recordings were stored digitally with a sampling rate of 44.1 kHz or 22.05 kHz and 16 bits/sample.

Recordings were transferred to a computer as WAV files, and signal processing was performed using MATLAB 7.1 (a registered trademark of The Mathworks, Inc.). The waveforms were down-sampled to 16 kHz for the purposes of cepstral analysis. To remove 60-Hz noise present in some recordings, a high-pass Butterworth filter (10th order) with cutoff frequency of 70 Hz was applied to each down-sampled waveform. The sentences were recorded in a continuous manner and later parsed into separate WAV files, one for each sentence, which included arbitrary silence before and after each utterance. The silence regions at the beginning and end of each WAV file were removed automatically by endpoint trimming. The power envelope of each WAV file signal was constructed using a 50-ms exponential moving average filter, then the regions at the beginning and end of each WAV file that were more than 25 dB below the envelope peak were trimmed. The trimmed WAV files were analyzed using the ITU-T P.56 standard, Method B ("Objective measurement of active speech level," ITU-T Recommendation P.56, 2011), to measure the active speech level (ASL) which measured the signal level in active (non-silence) regions of speech. The ITU-T P.56 also measured the activity factor (AF) which was the fraction of time that speech was active in the trimmed WAV files. Endpoint trimming ensured that arbitrary silence before and after the speech utterance within a WAV file did not affect the AF or any other acoustic measures.

Vocal tract settings were estimated using HFCCs, which were designed to represent the vocal tract transfer function with invariance towards source characteristics (e.g., fundamental frequency, voice quality). In the HFCC algorithm of an embodiment of the invention, pre-emphasis ($\alpha=0.95$) was first applied to each WAV file signal. Next, a spectrogram of the signal was constructed using 20-ms Hamming windows, 1024-point fast Fourier Transforms (FFTs), and a frame rate of 100 frames/s. The log-power for each frame was calculated directly from the spectrogram square-magnitude as the base-10 log of the mean of the spectrogram across frequency. A perceptually inspired filter bank of 30 filters in the range 70 Hz to 7000 Hz was applied to the spectrogram magnitude, and filter output was log-compressed and transformed via the discrete cosine transform to the cepstral domain. The log power for each frame was combined with 12 transformed features to form a vector of 13 cepstral coefficients for each frame. Cepstral mean subtraction was applied to the set of cepstral vectors extracted from each trimmed WAV file, which subtracts from each coefficient the mean of coefficients across frames. First-order temporal derivatives of HFCCs (delta coefficients) were calculated using a delta size of 1 frame.

HFCC analysis produced a matrix of coefficients for each WAV file with a size of 13 coefficients×L frames, where L was approximately 200 frames. The matrix of cepstral coefficients (and delta coefficients) was reduced to a scalar measure by calculating the standard deviation sum across coefficients. A cepstral coefficient measure was devised based on the observation that a large articulation range means that speech articulators move a large distance from their rest positions during speech generation, thus producing a wide range of vocal tract settings and transfer functions. Since HFCCs represent vocal tract transfer functions, a wide range of vocal tract transfer functions translates into a wide range of HFCC values. The range of HFCC values was quantified with the standard deviation metric; and range measures were reduced to a scalar value by summing the standard deviation terms. The standard deviation metric can be used to quantify the range of the fundamental frequency ($F_0$) and log intensity envelope. Table I summarizes the analysis of the WAV files and HFCC measures by presenting the ASL and HFCC analysis of normal and PD speech, mean±standard deviation, N=380 sentences.

TABLE I

| Factor | Normal | PD |
| --- | --- | --- |
| Total duration, s | 1.99 ± 0.40 | 2.34 ± 0.94 |
| AF | 0.97 ± 0.03 | 0.95 ± 0.07 |
| Active duration, s | 1.93 ± 0.38 | 2.18 ± 0.62 |
| HFCC measure | 7.95 ± 0.50 | 6.66 ± 0.53 |
| ΔHFCC measure | 5.64 ± 0.56 | 4.40 ± 0.46 |

As shown in Table I, the WAV files of normal speech were shorter in duration (t(758)=6.68, p<0.0001) on average than that of PD speech and had a higher activity factor (4758)=5.12, p<0.0001). The "activity factor" refers to the percentage of time the speech signal is considered "active" (i.e., not a pause). Active duration (duration×AF) was also shorter (4758)=6.70, p<0.0001) on average for normal speech compared to PD speech, meaning that PD speech:

1) contained more inactivity (pauses), and
2) took longer to produce the same active speech material (lower speaking rate).

The cepstral coefficient measure (t(758)=34.5, p<0.0001) and delta coefficient measure (t(758)=33.4, p<0.0001) of normal speech were significantly larger than that of PD speech.

To measure the sensitivity of the measures, "leave-one-talker-out" classification experiments were performed. For each of the 78 talkers in the speech database, data from one talker was used for testing while data from the remaining talkers was used to train two classification models: one model for normal talkers and one model for PD talkers. Gaussian likelihood functions were used to model the statistical distributions of the articulation measures. For models with multiple inputs, full covariance matrices were used in the models. After training the models, the test data from the remaining talker was applied to the two models to produce likelihoods which were converted to class probabilities using Bayes' Law assuming equal a priori probabilities. The model with the largest probability was the output of the classifier and was compared to the known class (normal or PD) of the model data to tabulate classifier accuracy. The classification experiment was repeated for each of the 78 talkers, and classifier accuracy was tabulated for test speakers and also on the training data to assess how well the classifier generalized to novel speakers.

Results of the classification experiment are summarized in Table II. Data for each test talker included 10 sentences, so accuracy for each talker was calculated as the average percent correct over 10 sentences. For the training data, accuracy was calculated over the remaining 770 sentences. The results in Table II are the mean±standard deviation (a), N=76, calculated from the above averages over the 78 test talkers. Median accuracy for the test data was 100%, but average accuracy was lower and the standard deviation was relatively large. The standard deviation for the training data was much smaller because the mean accuracy was calculated over a much larger number of sentences.

TABLE II

| Model input | Test (%) | Train (%) |
| --- | --- | --- |
| HFCC σ sum | 90.1 ± 20 | 90.4 ± 0.3 |
| HFCC σ sum, combined | 92.1 ± 27 | 92.2 ± 0.6 |
| HFCC σ sum, concatenated | 92.1 ± 27 | 92.1 ± 0.4 |
| ΔHFCC σ sum | 88.8 ± 21 | 88.8 ± 0.3 |
| ΔHFCC σ sum, combined | 94.7 ± 22 | 94.7 ± 0.3 |
| ΔHFCC σ sum, concatenated | 93.4 ± 25 | 94.7 ± 0.4 |
| ΔΔHFCC σ sum | 85.8 ± 22 | 85.9 ± 0.3 |
| ΔΔHFCC σ sum, combined | 89.5 ± 31 | 90.6 ± 0.7 |
| ΔΔHFCC σ sum, concatenated | 89.5 ± 31 | 89.6 ± 1.0 |
| [HFCC, ΔHFCC] σ sum | 92.9 ± 18 | 93.1 ± 0.3 |
| [HFCC, ΔHFCC] σ sum, combined | 93.4 ± 25 | 93.4 ± 0.4 |
| [HFCC, ΔHFCC] σ sum, concatenated | 93.4 ± 25 | 93.5 ± 0.6 |

The results labeled "combined" refer to the combination of model likelihoods from all 10 sentences for each talker to form a single joint likelihood. Each sentence was assumed independent for each talker, so the joint likelihood for each talker was calculated as the product of the likelihoods for each sentence for each talker. The purpose of combining sentences from a talker was to increase the amount of data available to make a classifier decision, which should increase classifier accuracy. The results labeled "concatenated" refer to the concatenation of HFCC feature matrices from all 10 sentences for each talker before calculating the standard deviation for each cepstral coefficient. Thus, each talker in the test set and training set was represented by 1 feature set instead of 10. The purpose of concatenation was to increase the amount of data available to estimate HFCC standard deviations, reducing the variance of those estimates and increasing classifier accuracy. Experiments with concatenated data made it possible to more easily compare PD discrimination accuracy using short sentences (~2 s) versus longer, more phonetically balanced read passages (~20 s).

Figure 8:
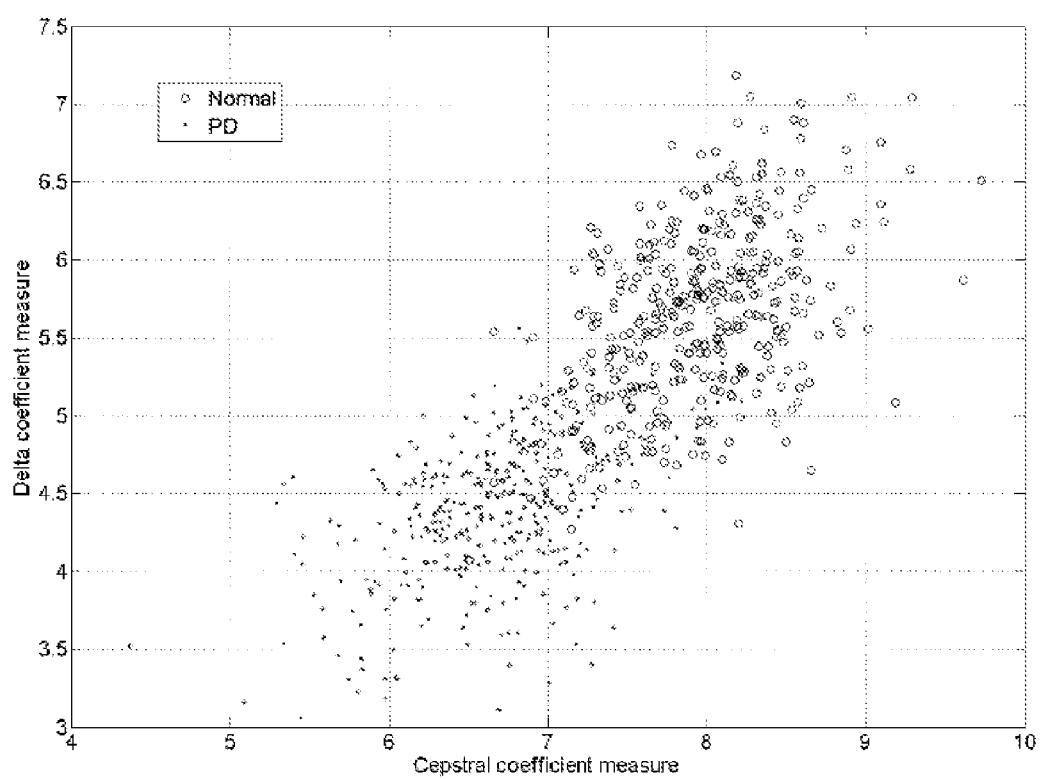
FIG. 8 shows cepstral coefficient measures versus delta coefficient measures for normal and PD talkers. Each point represents the measures from one sentence utterance.

The test-train mismatch for the models listed in Table II was less than 0.3%, except for two models that exhibited test-train mismatch less than 1.3%, which demonstrated good generalization to novel test talkers for the given data set. Results for the "combined" models indicated a modest increase in accuracy over results for individual sentences, demonstrating the benefits of combining information from all 10 sentences before forming a classifier decision. Results for the "concatenated" models showed no significant difference from the "combined" models, indicating that the two methods for increasing the amount of information used in making a classifier decision had about the same effect. The correlations of cepstral coefficient measure and delta coefficient measure were moderate: $r(378)=0.47$, $p<0.0001$ for normal speech and $r(378)=0.47$, $p<0.0001$ for PD speech. FIG. 8 shows the relationship between the cepstral coefficient measure and the delta coefficient measure for each group of talkers.

The delta coefficient measure may be compared with trimmed duration of stimuli as the two are related. In particular, for sentence material with a fixed number of words, a higher rate of change of cepstral coefficients corresponds to a shorter trimmed duration. A linear regression between the delta coefficient measure (cepstral coefficient change per frame) and the inverse of trimmed duration (1/s) was performed for each group of talkers. Note that frame rate was 100 frames/s, and both quantities had units of inverse time. For PD talkers, THFCC σ sum was a significant predictor ($\beta=0.110$, $t(377)=8.91$, $p<0.0001$) but not the constant term ($\alpha=-0.0174$, $t(377)=0.319$, $p>0.05$), and THFCC σ sum explained a significant proportion of variance ($R2=0.174$, $F(1,377)=79.4$, $p<0.0001$). For normal talkers, THFCC σ sum was a significant predictor ($\beta=0.0717$, $t(377)=8.71$, $p<0.001$) as was the constant term ($\alpha=0.117$, $t(377)=2.51$, $p<0.02$), and THFCC σ sum explained a significant proportion of variance ($R2=0.167$, $F(1,377)=75.8$, $p<0.0001$). For both groups, the regressions were statistically significant but modest, with the delta coefficient measure explaining only about 17% of the variance of inverse trimmed sentence duration.

The results in Table II are based on classification models with 1 or 2 input features, and accuracy on the test dataset and training dataset were in agreement, demonstrating trained models whose performance generalized well to novel talkers.

Several variations of HFCCs with up to 26 inputs were tested to explore the generalizability of the cepstral coefficient measure model and to gauge the effects of model size on accuracy mismatch between test set data and training set data. All experiments used a Gaussian function with full covariance matrix to model the likelihood distribution of each group, and a priori probability was assumed equal for the two groups. For all experiments, 10 of the 780 data points (from a single talker) were used to compute test accuracy, and the remaining 770 data points were used to compute training accuracy. Table III summarizes the results. In particular, Table III presents results for a leave-one-out accuracy on test data and training data for models of various dimensions. Accuracy values are mean±standard deviation.

TABLE III

| Model input | Dimension | Test (%) | Train (%) | Diff. (%) |
|---|---|---|---|---|
| HFCC σ sum | 1 | 90.1 ± 19.8 | 90.4 ± 0.25 | 0.3 |
| ΔHFCC σ sum | 1 | 88.8 ± 20.7 | 88.8 ± 0.31 | 0.0 |
| ΔΔHFCC σ sum | 1 | 85.8 ± 22.3 | 85.9 ± 0.33 | 0.1 |
| [HFCC, ΔHFCC] σ sum | 2 | 92.9 ± 18.4 | 93.1 ± 0.28 | 0.2 |
| HFCC σ | 13 | 87.1 ± 21.7 | 92.6 ± 0.35 | 5.5 |
| HFCC $\sigma^2$ | 13 | 84.5 ± 25.1 | 89.8 ± 0.33 | 5.3 |
| ΔHFCC σ | 13 | 86.6 ± 17.8 | 91.4 ± 0.31 | 4.8 |
| ΔΔHFCC σ | 13 | 84.9 ± 19.8 | 88.1 ± 0.33 | 3.2 |
| [HFCC, ΔHFCC] σ | 26 | 88.7 ± 17.7 | 95.4 ± 0.31 | 6.7 |

When the number of inputs (dimension) was 1 or 2, test-train difference was less than 0.3%. However, when all 13 cepstral coefficients standard deviations were inputs to the classifier, test-train difference varied from 3.2% to 5.5%, and test-train difference was greatest at 6.7% when a 26-input model was employed.

Because none of the 13-input models outperformed the 2-input model in accuracy on the training data, it can be assumed that the distribution normality was more accurate for the accumulated standard deviation sum than for the standard deviation of the individual cepstral coefficients.

The test-train mismatch results in Table III highlight the modeling issues of input dimension and generalization. Using data from 760 sentences by 76 talkers, the Gaussian models in the leave-one-talker-out experiments generalized well with 2 inputs but not with 13 inputs.

Without evidence of generalization, models are susceptible to over-training and "memorizing" the training data instead of converging to the underlying process under investigation, which occurs when a model has too many inputs (too many degrees of freedom) for a given amount of training data. Results derived using overtrained models may be accurate for the particular dataset employed in the experiment but grossly misleading for the greater population of talkers in general. Generalization may be tested by splitting a dataset into test data and training data (which may be further split to include a validation set for iterative training or feature selection). A cross-validation training paradigm that separates data by talker is important because training and testing speech models using data from the same talker can significantly over-estimate model accuracy, due to the weakness of the assumption that different data samples from the same talker are independent. Such an assumption is particularly weak when the dataset consists of the same talker producing repeated samples of the same stimulus, such as /a/ or other sustained vowels. Analysis with the ITU-T P.56 standard, Method B, which was designed to measure speech level in recordings containing significant pauses (e.g., telephony), revealed that not only were the sentence utterances significantly longer in duration and the activity factor significantly lower for PD talkers, duration of active speech (duration×activity factor) and duration of pauses were also significantly longer for PD talkers. Also, the delta coefficient measure significantly correlated with inverse sentence duration, which can provide a proxy for articulation rate. These results demonstrate the validity of sentence material for PD speech analysis for duration measures using the ASL algorithm and for articulation characteristics using the cepstral measures.

In the ASL algorithm used in an embodiment of the invention, an energy envelope is used in separating active speech from pauses and includes a "hangover" region of 200 ms during which time the energy envelope must remain below before the algorithm signals a transition from active speech to a pause. Use of HFCCs, a cepstral coefficient variant, in studying the acoustic measures of PD speech provides better correlation than MFCCs as an acoustic measure of PD because of how filter bandwidth is determined. HFCCs decouple filter bandwidth from the design of the filter bank and set bandwidth according to filter center frequency using perceptually inspired bandwidth of critical bands. A consequence of having filter bandwidth as a free parameter is the ability to vary bandwidth beyond the perceptually inspired values. In the context of PD speech analysis, the effects of dysphonia may be seen as noise in voiced speech, so varying HFCC filter bandwidth provides insight into the relative contribution of variation of cepstral coefficients due to articulation and the effects of dysphonia.

Many possible methods exist for extracting information from HFCC matrices for the purposes of characterizing PD speech and discriminating PD and normal speech. Simple second-order measures that reduced the HFCC matrices to scalars may be used to simplify modeling, however, more sophisticated models with HFCC matrices as input may lead to greater insight into the characteristics of PD speech. Furthermore, HFCC measures may be combined with voicing and prosody measures in acoustic models to increase the amount of information drawn upon to identify PD speech and also to distinguish PD speech from other types of dysarthrias.

By using acoustic measures sensitive to indicia of PD, automated PD detection can be accomplished. The acoustic measure described herein provides a sensitivity to articulation range and rate and involves calculating the standard deviation sums of cepstral coefficients and delta coefficients which are sensitive to articulation range and rate, respectively. The measure was designed to operate on read speech as short as 2 seconds in duration. The measure was designed to be a robust algorithm that does not require boundary detection (phonemes, syllables, words, or voiced-unvoiced-silence boundaries) and does not require phonetic analysis.

As illustrated by the experimental results, articulation measures from read or spontaneous speech can provide insight into the effects of PD on speech and may be more effective in certain cases than voicing measures. Because articulation involves more degrees of freedom than steady-state phonation, articulation errors (independently or in conjunction with voicing errors) may allow for greater accuracy in acoustically detecting PD than voicing alone. Moreover, articulation errors due to PD may be more specific than alterations to the steady state phonation signal, producing a detector of higher specificity. That is, many diseases affect voice production similarly, but PD may affect articulation in specific ways that allow for greater differentiation between PD and other acquired speech disorders. Although this example is specific to PD embodiments are applicable to other diseases.

All patents, patent applications, provisional applications, and publications referred to or cited herein are incorporated by reference in their entirety, including all figures and tables, to the extent they are not inconsistent with the explicit teachings of this specification.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

It should be understood that the examples and embodiments described herein are for illustrative purposes only and that various modifications or changes in light thereof will be suggested to persons skilled in the art and are to be included within the spirit and purview of this application.

What is claimed is:

1. A method for screening for diseases, the method comprising: performing a signal analysis of a speech sample received from a subject, the signal analysis comprising extracting human factor cepstral coefficients from the speech sample and identifying articulation range and articulation rate using the human factor cepstral coefficients extracted from the speech sample, and analyzing language patterns, wherein the analyzing of the language patterns comprises analyzing the language patterns to determine if an indicator of a neurological disease is present;
   determining a likelihood and type of a disease based upon the articulation range and articulation rate identified by the signal analysis of the speech sample, as well as the analyzing of the language patterns; and
   outputting information indicating the likelihood and type of the disease.

2. The method of claim 1, wherein identifying the articulation range and articulation rate using the human factor cepstral coefficients extracted from the speech sample comprises:
   calculating standard deviation sums of the cepstral coefficients to estimate the articulation range; and
   calculating delta coefficients of the speech sample to estimate the articulation rate.

3. The method of claim 1, wherein extracting the human factor cepstral coefficients from the speech sample comprises:
   constructing a spectrogram of a signal of the speech sample;
   calculating a log-power for each frame from the spectrogram;
   applying a filter to a magnitude of the log-power;
   performing a log-compression and transform to a cepstral domain of an output of the filter; and
   forming a vector of cepstral coefficients for each frame.

4. The method of claim 1, wherein the signal analysis of the speech sample does not involve performing boundary detection or phonetic analysis.

5. The method of claim 1, wherein determining the likelihood and type of the disease based upon the articulation range and articulation rate identified by the signal analysis of the speech sample comprises using the articulation range and articulation rate to determine a likelihood of Parkinson's Disease for the subject.

6. The method according to claim 5, wherein determining the likelihood of Parkinson's disease comprises:
   comparing the articulation range and articulation rate of the speech sample with normative baseline acoustic measures for Parkinson's disease to generate values indicating the likelihood of Parkinson's disease for the subject.

7. The method according to claim 1, wherein determining the likelihood and type of the disease based upon the articulation range and articulation rate identified by the signal analysis of the speech sample comprises:
  comparing the articulation range and articulation rate of the speech sample with previously obtained measures from the same subject to generate values indicating the likelihood of Parkinson's disease for the subject.

8. The method according to claim 1, wherein determining the likelihood and type of the disease based upon the articulation range and articulation rate identified by the signal analysis of the speech sample comprises:
  comparing the articulation range and articulation rate of the speech sample with corresponding measures obtained from a set of other speakers to generate values indicating the likelihood of Parkinson's disease for the subject.

9. The method of claim 1, wherein the speech sample is about 2 seconds in duration.

10. The method of claim 1, wherein the speech sample is received from an outgoing call of the subject received through a telephony, voice over internet protocol (VoIP) or cellular service provider.

11. The method of claim 1, wherein the speech sample is received as a recorded speech sample uploaded to a network via a website interface.

12. The method of claim 1, wherein the speech sample is received directly from a microphone.

13. The method according to claim 1, further comprising:
  performing a pre-processing of the speech sample to clean the speech sample or select segments of the speech sample before performing the signal analysis.

14. A system for screening for a disease, the system comprising:
  an application service provider for receiving a speech sample from a subject;
  a memory for receiving and storing the speech sample; and
  one or more computer-readable storage media in operable communication with the memory and having stored thereon computer-executable instructions comprising:
  a pre-processing module for receiving the speech sample from the application service provider and cleaning the speech sample or selecting segments of the speech sample for further processing;
  a speech metric module for receiving the speech sample from the pre-processing module and identifying articulation range and articulation rate using human factor cepstral coefficients; and
  a language marker module for receiving the speech sample from the pre-processing module and analyzing language patterns;
  a comparator for comparing the output of the speech metric module and the output of the language marker module with normative data, criteria, or previous output of the speech metric module and the language marker module stored in the memory of the system and outputting a decision indicating a likelihood of a neurological disease.

15. The system of claim 14, wherein the speech metric module identifies the articulation range and articulation rate using the human factor cepstral coefficients by:
  calculating standard deviation sums of the cepstral coefficients to estimate the articulation range; and
  calculating delta coefficients of the speech sample to estimate the articulation rate.

16. The system of claim 14, wherein the speech metric module extracts the human factor cepstral coefficients from the speech sample and uses the extracted human factor cepstral coefficients to identify the articulation range and articulation rate.

17. The system of claim 16, wherein the speech metric module extracts the human factor cepstral coefficients from the speech sample by:
  constructing a spectrogram of a signal of the speech sample;
  calculating a log-power for each frame from the spectrogram;
  applying a filter to a magnitude of the log-power;
  performing a log-compression and transform to a cepstral domain of an output of the filter; and
  forming a vector of cepstral coefficients for each frame.

18. The system of claim 14, wherein the identifying articulation range and articulation rate using human factor cepstral coefficients does not involve performing boundary detection or phonetic analysis.

19. The system of claim 14, wherein the disease is Parkinson's disease.

* * * * *

UNITED STATES PATENT AND TRADEMARK OFFICE
CERTIFICATE OF CORRECTION

PATENT NO. : 9,579,056 B2
APPLICATION NO. : 14/435969
DATED : February 28, 2017
INVENTOR(S) : John Clyde Rosenbek et al.

It is certified that error appears in the above-identified patent and that said Letters Patent is hereby corrected as shown below:

In the Specification

Column 19,
Lines 65-66, "factor (4758)," should read --factor ($t(758)$)--

Column 20,
Line 2, "shorter (4758)," should read --shorter ($t(758)$)--

Column 20,
Line 37, "deviation (a)," should read --deviation ($\sigma$)--

Column 21,
Line 42, "THFCC a sum," should read --THFCC $\sigma$ sum--

Column 21,
Line 44, "THFCC a sum," should read --THFCC $\sigma$ sum--

Column 22,
Line 54, "such/as/or," should read --such as /a/ or--

Column 22,
Line 60, "(duration×activity factor)," should read --(duration × activity factor)--

Signed and Sealed this
Twenty-ninth Day of August, 2017

Joseph Matal
*Performing the Functions and Duties of the
Under Secretary of Commerce for Intellectual Property and
Director of the United States Patent and Trademark Office*